(12) United States Patent
Aimi et al.

(10) Patent No.: US 11,058,296 B2
(45) Date of Patent: Jul. 13, 2021

(54) OPHTHALMOLOGIC IMAGE DISPLAY DEVICE AND OPHTHALMOLOGIC IMAGING DEVICE

(71) Applicant: TOPCON CORPORATION, Tokyo (JP)

(72) Inventors: Taiki Aimi, Tokyo (JP); Masahiro Akiba, Tokyo (JP); Atsushi Kubota, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 215 days.

(21) Appl. No.: 16/061,021

(22) PCT Filed: Oct. 25, 2016

(86) PCT No.: PCT/JP2016/081583
§ 371 (c)(1),
(2) Date: Jun. 11, 2018

(87) PCT Pub. No.: WO2017/098824
PCT Pub. Date: Jun. 15, 2017

(65) Prior Publication Data
US 2018/0360308 A1    Dec. 20, 2018

(30) Foreign Application Priority Data
Dec. 10, 2015   (JP) .............................. JP2015-240988

(51) Int. Cl.
*A61B 3/10*   (2006.01)
*A61B 3/00*   (2006.01)
(Continued)

(52) U.S. Cl.
CPC ............ *A61B 3/102* (2013.01); *A61B 3/0025* (2013.01); *A61B 3/0033* (2013.01);
(Continued)

(58) Field of Classification Search
CPC ......... A61B 3/14; A61B 3/102; A61B 3/0025; A61B 3/12; A61B 3/1025; A61B 3/0008;
(Continued)

(56) References Cited

U.S. PATENT DOCUMENTS

| 2007/0276269 A1 | 11/2007 | Yun et al. |
| 2009/0005691 A1 | 1/2009 | Huang et al. |

(Continued)

FOREIGN PATENT DOCUMENTS

| JP | 2008-073099 A | 4/2008 |
| JP | 2009536740 A | 10/2009 |

(Continued)

OTHER PUBLICATIONS

Extended European Search Report dated Jun. 26, 2019 in European Application No. 16872724.6.
(Continued)

*Primary Examiner* — Collin X Beatty
*Assistant Examiner* — Grant A Gagnon
(74) *Attorney, Agent, or Firm* — Xsensus LLP

(57) ABSTRACT

A storage device of an ophthalmologic image display device of an embodiment stores a three dimensional data set acquired by scanning a subject's eye using OCT. An image processor forms, based on the three dimensional data set, a B-mode image, front images, and composite front image obtained from the front images. A display controller displays the B-mode image, front images and composite front image in a predetermined layout. The display controller displays distinguishment color information for distinguishment between the front images by colors and slice area information that indicates a partial region of the B-mode image corresponding to a slice area of the three dimensional data set represented by each front image in a color according to the distinguishment color information, and displays a com- (Continued)

posite front image based on the front images, each of which is expressed by a color according to the distinguishment color information.

15 Claims, 6 Drawing Sheets

(51) Int. Cl.
    *A61B 3/14*         (2006.01)
    *G06T 19/20*      (2011.01)
    *A61B 3/12*         (2006.01)
    *A61B 3/135*      (2006.01)

(52) U.S. Cl.
    CPC .......... *A61B 3/0041* (2013.01); *A61B 3/0058* (2013.01); *A61B 3/1233* (2013.01); *A61B 3/135* (2013.01); *A61B 3/14* (2013.01); *G06T 19/20* (2013.01); *G06T 2210/41* (2013.01); *G06T 2219/028* (2013.01); *G06T 2219/2012* (2013.01)

(58) Field of Classification Search
CPC ..... A61B 3/1005; A61B 3/113; A61B 3/1225; A61B 3/0058; A61B 3/107; A61B 3/117; A61B 3/13; A61B 3/1015; A61B 3/145; A61B 3/10; A61B 3/0041; A61B 3/152; A61B 3/103; A61B 3/0033; A61B 3/0075; A61B 3/0091; A61B 3/112; A61B 3/18; A61B 5/0066; A61B 2576/02; A61B 3/005; A61B 3/101; A61B 3/1208; A61B 3/1241; A61B 3/125; A61B 3/158; A61B 5/0013; A61B 2560/0475; A61B 3/00; A61B 3/0083; A61B 3/028; A61B 3/032; A61B 3/11; A61B 3/111; A61B 3/1233; A61B 3/132; A61B 5/0075; A61B 5/163; A61B 5/489; A61B 2017/00716; A61B 2503/10; A61B 2503/20; A61B 2560/0223; A61B 2560/0228; A61B 2560/0233; A61B 2560/0266; A61B 2560/0271; A61B 3/0016; A61B 3/024; A61B 3/063; A61B 3/08; A61B 3/1035; A61B 3/1173; A61B 3/1176; A61B 3/1216; A61B 3/135; A61B 3/15; A61B 3/154; A61B 3/156; A61B 5/0022; A61B 5/0059; A61B 5/02416; A61B 5/0261; A61B 5/1075; A61B 5/1079; A61B 5/1103; A61B 5/1114; A61B 5/1116; A61B 5/1124; A61B 5/1128; A61B 5/1176; A61B 5/1455; A61B 5/165; A61B 5/18; A61B 5/4821; A61B 5/4848; A61B 5/486; A61B 5/6803; A61B 5/7275; A61B 5/7425; A61B 8/10; A61B 90/20; G06T 2207/30041; G06T 7/0012; G06T 2207/10101; G06T 7/0016; G06T 2200/24; G06T 7/74; G06T 11/003; G06T 2207/10016; G06T 2207/10056; G06T 2207/20016; G06T 2207/20056; G06T 2210/41; G06T 3/4038; G06T 7/0014; G06T 7/11; G06T 7/246; G06T 7/30; G06T 7/32; G06T 7/337; G06T 7/64
USPC ........................................................ 351/206
See application file for complete search history.

(56) References Cited

U.S. PATENT DOCUMENTS

| | | |
|---|---|---|
| 2011/0243408 A1 | 10/2011 | Takama |
| 2012/0050308 A1 | 3/2012 | Nakano et al. |
| 2012/0316434 A1 | 12/2012 | Yun et al. |
| 2013/0301008 A1 | 11/2013 | Srivastava et al. |
| 2014/0300863 A1 | 10/2014 | Fukuma et al. |
| 2014/0300864 A1 | 10/2014 | Fukuma et al. |
| 2014/0300866 A1 | 10/2014 | Fukuma et al. |
| 2014/0320809 A1 | 10/2014 | Fukuma et al. |
| 2014/0320810 A1 | 10/2014 | Fukuma et al. |
| 2015/0092195 A1 | 4/2015 | Blatter et al. |
| 2016/0317029 A1 | 11/2016 | Srivastava et al. |
| 2016/0367132 A1 | 12/2016 | Yun et al. |

FOREIGN PATENT DOCUMENTS

| | | |
|---|---|---|
| JP | 2010-142498 A | 7/2010 |
| JP | 2010523286 A | 7/2010 |
| JP | 2012-45298 A | 3/2012 |
| JP | 2013154120 A | 8/2013 |
| JP | 2014113207 A | 6/2014 |
| JP | 2014200680 A | 10/2014 |
| JP | 2015515894 A | 6/2015 |

OTHER PUBLICATIONS

International Search Report and Written Opinion for PCT Application PCT/JP2016/081583, dated Jan. 24, 2017, 10 pages including 2 pages of English Translation.
Xu Jing et al., "Real-time acquisition and display of flow contrast using speckle variance optical coherence tomography in a graphics processing unit", Journal of Biomedical Optics, vol. 19, No. 2, Feb. 6, 2014, pp. 026001-1-026001-5.
Zhang Qinqin et al., "Swept Source OCT Angiography of Neovascular Macular Telangiectasia Type 2", Retina, vol. 35, No. 11, Nov. 30, 2015, pp. 2285-2299.
Povazay Boris et al., "Wide-Field Optical Coherence Tomography of the Choroid In Vivo", Investigative Ophthalmology and Visual Science, vol. 50, No. 4, Apr. 3, 2009, pp. 1856-1863.
Japanese Office Action dated May 26, 2020 in Japanese Application No. 2015-240988.
Dae Yu Kim et al., "Optical imaging of the chorioretinal vasculature in the living human eye", Biological Imaging Center, California Institute of Technology, Pasadena, CA 91125; Department of Ophthalmology and Vision Science, University of California, Davis, Sacramento, CA 95817; and Department of Ophthalmology, University of California, San Francisco, CA 94143, pp. 14354-14359 | PNAS | Aug. 27, 2013 | vol. 110 | No. 35 www.pnas.org/cgi/doi/10.1073/pnas.1307315110.
Japanese Office Action dated Dec. 15, 2020, in corresponding Japanese Patent Application No. 2015-240988.

OPHTHALMOLOGIC IMAGE DISPLAY DEVICE AND OPHTHALMOLOGIC IMAGING DEVICE

CROSS-REFERENCE TO RELATED APPLICATIONS

This application is a national stage (under 35 U.S.C. 371) of International Patent Application No. PCT/JP2016/081583, filed Oct. 25, 2016, claiming priority to Japanese Patent Application No. 2015-240988, filed Dec. 10, 2015, both of which are herein incorporated by reference in their entirety.

FIELD

Embodiments described herein relate generally to an ophthalmologic image display device and an ophthalmologic imaging device.

BACKGROUND

Diagnostic imaging serves an important role in the field of ophthalmology. In recent years, utilization of optical coherence tomography (OCT) has advanced. OCT is being used not only for acquiring B-mode images and three dimensional images of a subject's eye but also for acquiring front images (or en-face images) such as C-mode images and shadowgrams. OCT is also utilized for acquiring images that emphasize a specific site of the subject's eye and acquiring functional information. For example, images in which retinal blood vessels and choroidal blood vessels are emphasized (i.e., angiograms) can be constructed based on time-series data acquired by OCT. Further, it is also possible to obtain blood flow information (e.g., blood flow velocity, blood flow amount) from phase information contained in time-series data acquired by OCT. Such imaging techniques are disclosed in, for example, Japanese Unexamined Patent Application Publication No. 2014-200680, Japanese Unexamined Patent Application Publication (Translation of PCT Application) No. 2015-515894, and Japanese Unexamined Patent Application Publication (Translation of PCT Application) No. 2010-523286.

SUMMARY OF THE INVENTION

Problem to be Solved by the Invention

In the ophthalmologic diagnostic imaging, a plurality of images is observed in a sequential manner, or a list of a plurality of images is observed, in general. Particularly in OCT diagnostic imaging, the user observes various types of images such as B-mode images, front images, morphological images, functional images, while changing slice positions, slice thicknesses, and slice areas as needed. However, it has been difficult to smoothly and promptly perform such observation with conventional techniques.

For example, according to the conventional technique capable of displaying a plurality of images one after another, it is necessary to display front images one by one while changing the depth positions in order for a user to observe sites of interest (e.g., a blood vessel, a lesion part, a layer tissue) at various depth positions of the eye fundus. Therefore, it has been difficult to comprehensively grasp the states of the sites of interest at various depth positions. On the other hand, according to the conventional technique capable of displaying a plurality of front images as a list, it is possible to grasp the states of the individual sites of interest at a plurality of depth positions. However, with this conventional technique, it has been impossible to easily grasp which areas of the subject's eye individual front images represent. In addition, it has been impossible to easily grasp the positional relationship between the front images. Moreover, it has also been difficult to grasp the comprehensive distribution of the sites of interest along the depth direction.

SUMMARY

A purpose of the ophthalmologic image display device and ophthalmologic imaging device according to the present embodiment is to make it possible for a user to easily and comprehensively grasp the states of the subject's eye at various depth positions.

An ophthalmologic image display device according to an exemplary embodiment includes a storage device, an image processor, and a display controller. The storage device stores a three dimensional data set acquired by scanning a subject's eye using optical coherence tomography. The image processor forms, based on the three dimensional data set, a B-mode image, a plurality of front images, and a composite front image obtained by composing the plurality of front images. The display controller displays the B-mode image, the plurality of front images and the composite front image in a predetermined layout on a display device. In addition, the display controller displays distinguishment color information for distinguishment between the plurality of front images by colors and slice area information that indicates a partial region of the B-mode image corresponding to a slice area of the three dimensional data set represented by each of the plurality of front images in a color according to the distinguishment color information, and displays a composite front image based on the plurality of front images, each of which is expressed by a color according to the distinguishment color information.

The embodiment makes it possible for a user to easily and comprehensively grasp the states of the subject's eye at various depth positions.

DETAILED DESCRIPTION

Figure 1:
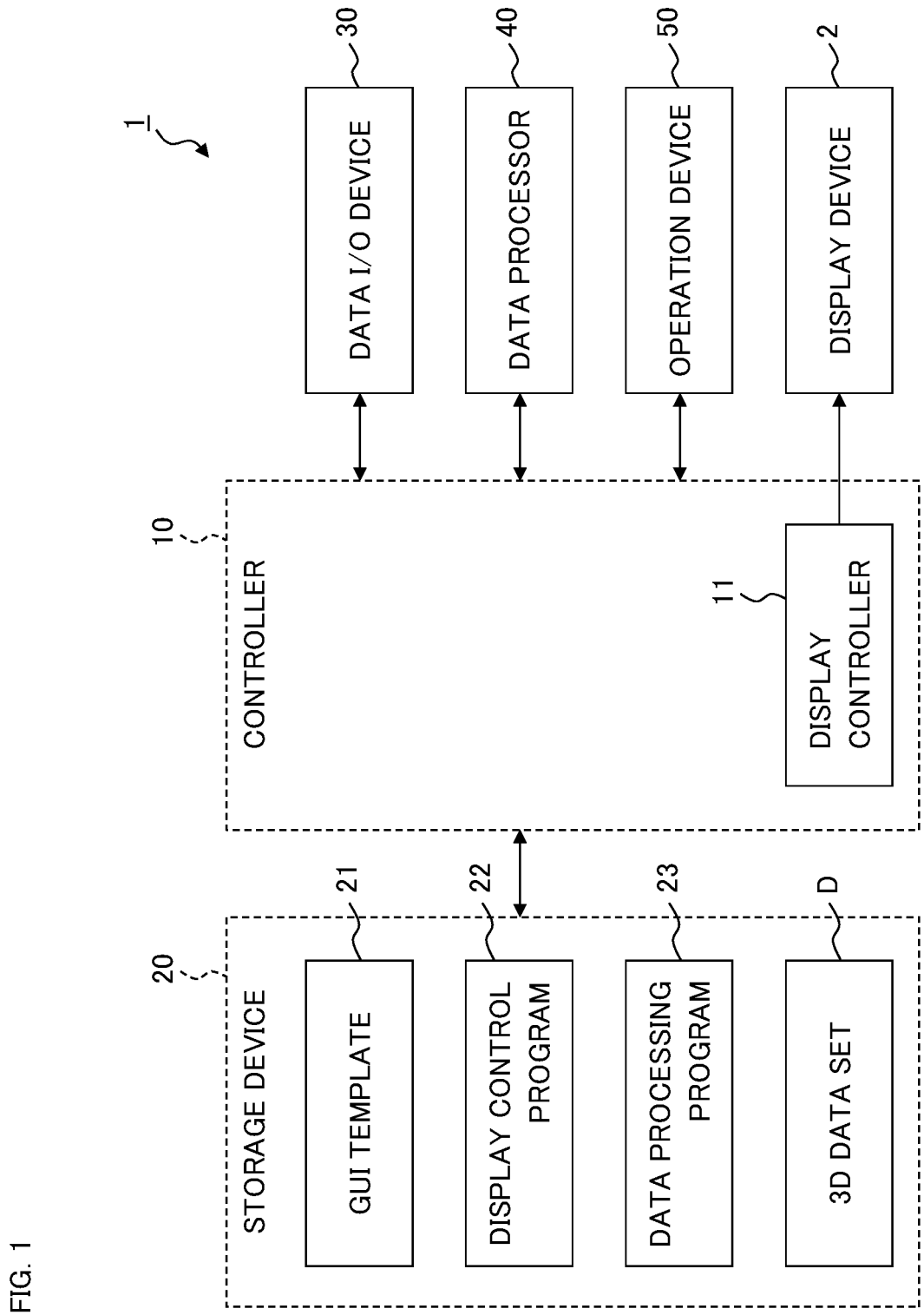
FIG. 1 is a schematic diagram illustrating an example of the configuration of an ophthalmologic image display device according to an embodiment.

Exemplary embodiments of the present invention will be described with referring to the drawings. It should be noted that any of the matters described in the documents cited in the present specification and any publicly known techniques can be incorporated into the present invention and embodiments thereof.

The embodiment provides a graphical user interface (GUI) for observing images of a subject's eye. The GUI is, at least, used for the observation of OCT images. Types of the OCT images include the followings: an image in an arbitrary cross section mode (e.g., a B-mode image, a C-mode image, a multi planar reconstruction (MPR) image); a shadowgram created by the projection of an arbitrary area of a three dimensional data set (e.g., volume data, stack data); and a blood vessel enhanced image (i.e., angiogram) formed based on a three dimensional data set composed from a plurality of two dimensional data sets obtained through iteratively scanning substantially the same area of the subject's eye. The three dimensional data set is constructed through the following steps, for example: scanning each of a plurality of B-cross sections B1, B2, . . . , Bn a predetermined number of times (e.g., four times); forming a predetermined number of B-mode images (e.g., four B-mode images) for each B-cross section Bi (i=1, 2, . . . , n); and embedding the B-mode images thus obtained in a single three dimensional coordinate system. Optionally, the B-mode images embedded in the three dimensional coordinate system are voxelized. Such an image forming technique is known.

The ophthalmologic image display device of the embodiment has a function of forming an image from a three dimensional data set, which is a rendering function realized by an image forming device. The ophthalmologic image display device obtains a three dimensional data set acquired by an ophthalmologic OCT apparatus via a network (e.g., in-house LAN) or a recording medium and renders the three dimensional data set according to an instruction from a user or a computer, thereby forming an image for observation. Note that the ophthalmologic image display device may or may not include a display device on which the image for observation is displayed.

In addition to the ophthalmologic image display device as described above, the ophthalmologic imaging device of the embodiment includes an optical system, a drive system, a control system, a data processing system, etc. for performing OCT. The ophthalmologic imaging device is configured to be capable of performing, for example, Fourier domain OCT. The Fourier domain OCT is also referred to as frequency domain OCT. Types of the Fourier domain OCT include spectral domain OCT and swept source OCT. The spectral domain OCT is a technique of imaging the subject's eye by acquiring the spectra of interference light in a space-divisional manner using a broadband low coherence light source and a spectrometer and applying Fourier transform to the spectra. The swept source OCT is a technique of imaging the subject's eye by acquiring the spectra of interference light by time-divisional manner using a wavelength sweep light source (also referred to as a wavelength tunable light source) and a photodetector (e.g., balanced photodiode) and applying Fourier transform to the spectra. The ophthalmologic imaging device may include a medical imaging modality other than OCT. Examples of such a medical imaging modality include a fundus camera, a scanning laser ophthalmoscope (SLO), a slit lamp microscope, and an ophthalmologic surgical microscope.

<Ophthalmologic Image Display Device>
[Configuration]

Figure 2:
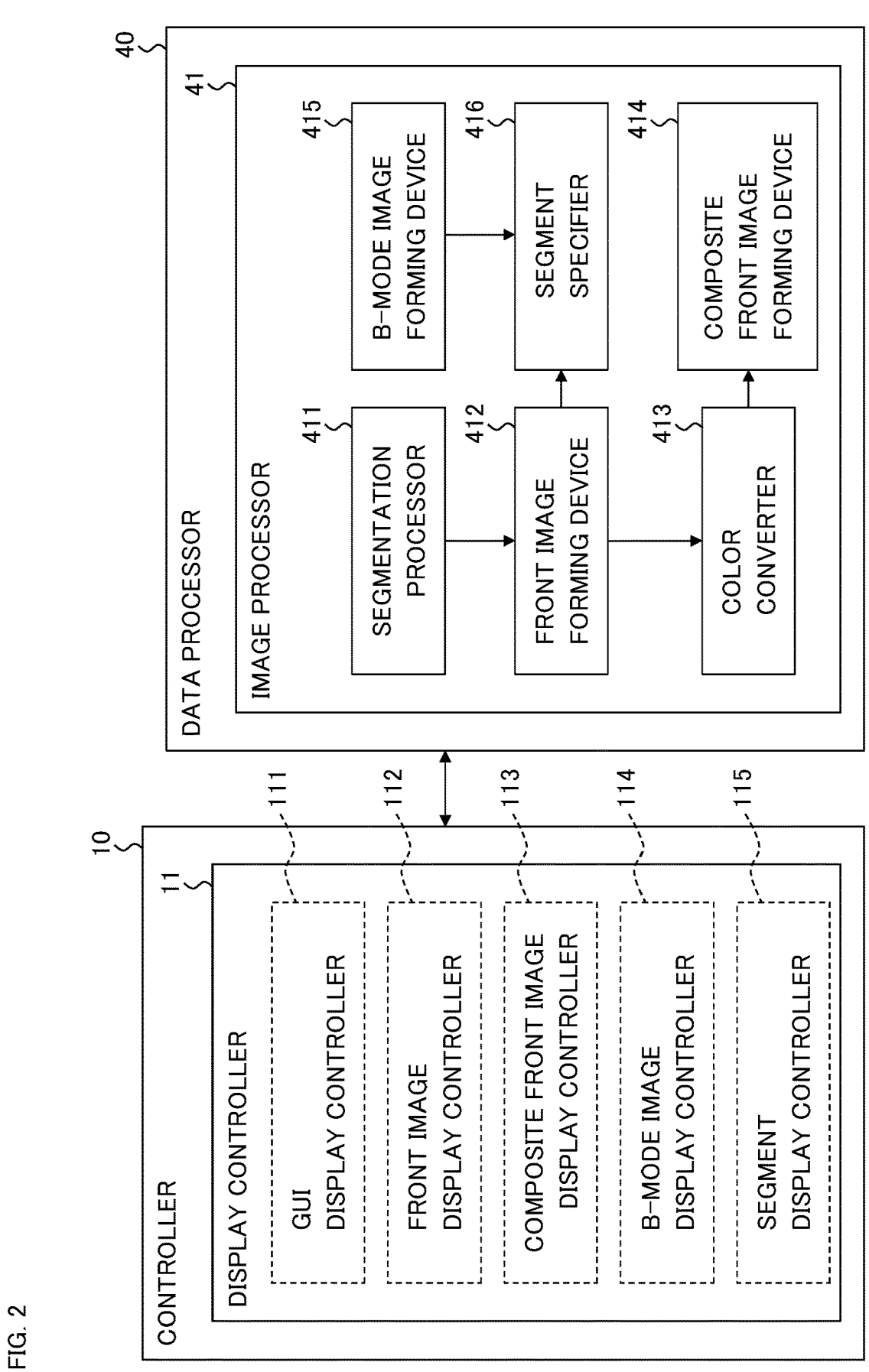
FIG. 2 is a schematic diagram illustrating an example of the configuration of the ophthalmologic image display device according to the embodiment.

An embodiment of an ophthalmologic image display device will be described. FIG. 1 and FIG. 2 show an exemplary configuration of the ophthalmologic image display device. The ophthalmologic image display device 1 controls the display device 2 to display a GUI for observing images of the subject's eye and various information related to the subject's eye. The display device 2 may be a part of the ophthalmologic image display device 1 or may be an external device connected to the ophthalmologic image display device 1.

The ophthalmologic image display device 1 includes the controller 10, the storage device 20, the data input and output device (data I/O device) 30, the data processor 40, and the operation device 50.

(Controller 10)

The controller 10 controls each part of the ophthalmologic image display device 1. The controller 10 includes a processor. In this specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The controller 10 realizes the functions according to the embodiment, for example, by reading out and executing a program stored in a storage circuit or a storage device (for example, the storage device 20).

The controller 10 includes the display controller 11. The display controller 11 performs control for the display device 2 to display information. The display controller 11 can perform the display control based on information stored in the storage device 20.

As shown in FIG. 2, the display controller 11 includes the GUI display controller 111, the front image display controller 112, the composite front image display controller 113, the B-mode image display controller 114, and the segment display controller 115.

Based on the GUI template 21 and the display control program 22 stored in the storage device 20, the GUI display controller 111 controls the display device 2 to display screens, dialogs, icons, and the like, which are utilized as GUIs.

Based on the display control program 22, the front image display controller 112 displays a front image such as a C-mode image, a shadowgram, or a blood vessel enhanced image (i.e., angiogram) on the GUI screen. In the present embodiment, a plurality of front images formed from the three dimensional data set D is displayed in respective display regions of the GUI screen. The display regions are predetermined. The details of such a display mode will be described later.

The composite front image display controller 113 displays a composite image of a plurality of front images of the subject's eye in a predetermined display region of the GUI screen. The composite image is hereinafter referred to as a composite front image. Note that the composite front image may be an image formed based on a single piece of image data or an image formed based on a plurality of pieces of image data. In the former case, the composite front image display controller 113 displays a composite front image formed by the data processor 40 on the GUI screen. In the latter case, the composite front image display controller 113 displays a plurality of images based on a plurality of pieces of image data one over another. Such display control is executed, for example, by using the layer display function. Specifically, the composite front image display controller 113 can perform processing of respectively displaying a plurality of images based on a plurality of pieces of image data in a plurality of layers, processing of setting the opacity (i.e., a value) of each layer, and processing of displaying these layers one over another.

The B-mode image display controller 114 displays a B-mode image formed from the three dimensional data set D in a predetermined display region of the GUI screen.

For each of the front images, the segment display controller 115 displays information that indicates the partial region of the B-mode image corresponding to the slice area (i.e., segment) of the three dimensional data set D represented by a concerned front image, on the GUI screen. Such information is hereinafter referred to as segment information. The segment information is displayed in the color assigned to the corresponding front image.

A specific example of processing performed by the display controller 11 (e.g., the GUI display controller 111, the front image display controller 112, the composite front image display controller 113, the B-mode image display controller 114, and the segment display controller 115) will be described later.

(Storage Device 20)

Various kinds of information is stored in the storage device 20. In the present embodiment, the storage device 20 stores the GUI template 21, the display control program 22, the data processing program 23, and the three dimensional data set D.

The GUI template 21 includes templates of screens, dialogs, icons, and the like, which are displayed as GUIs on the display device 2.

The display control program 22 includes a program executed for the controller 10 to perform control relating to GUI displayed based on the GUI template 21. In the present embodiment, the display control program 22 includes a program for the display controller 11 to perform control for displaying GUIs and images. The display control carried out in the present embodiment is realized by cooperation of hardware (i.e., a processor) and software, that is, cooperation of the display controller 11 and the display control program 22. A specific example of the display processing will be described later.

The data processing program 23 includes a program executed for the data processor 40 (and the controller 10) to perform various kinds of data processing. The data processing executed by the present embodiment is realized by cooperation of hardware (i.e., a processor) and software, that is, cooperation of the data processor 40 (and the controller 10) and the data processing program 23. A specific example of the data processing will be described later.

The three dimensional data set D will be described. The three dimensional data set D is image data representing the state (e.g., morphology, structure, form, shape, function) of the three dimensional region of the subject's eye. The three dimensional data set D may include image data in which positions of image elements (e.g., pixels, voxels) are defined by a three dimensional coordinate system. Examples of such image data include stack data and volume data. Stack data is image data that is formed by embedding two or more pieces of B-mode image data in a three dimensional coordinate system. Volume data is image data that is formed by converting pixels of stack data into voxels. Another example of the three dimensional data set D may include a group of B-mode image data whose pixel positions are defined by a two dimensional coordinate system. As still another example, the three dimensional data set D may be time-series image data or may be image data constructed from time-series image data. Examples of such image data include three dimensional image data in which blood vessels are emphasized (i.e., a three dimensional angiogram), and image data representing blood flow dynamics in a plurality of vertical cross sections (i.e., B-scan planes) or in a three dimensional region. The type of the three dimensional data set D is arbitrary, and the three dimensional data set D is formed using a known OCT technique corresponding to the type thereof.

The three dimensional data set D formed by the ophthalmologic OCT apparatus (or by the computer that processes the data acquired by the ophthalmologic OCT apparatus) is transmitted to and stored in an image management server installed in a health facility, a network, or the like, for example. Supplementary information is associated with the three dimensional data set D. The supplementary information includes subject identification information (e.g., patient ID), identification information of left eye or right eye, imaging date and time, health facility identification information, and the like. As a specific example of its implementation, the three dimensional data set D is managed with a file format conformable to the digital imaging and communications in medicine (DICOM) standard, and at least part of the supplementary information is included in DICOM tag information. Alternatively, the three dimensional data set D may be managed in association with the electronic medical record of the subject. In response to reception of a request from the ophthalmologic image display device 1, the image management server retrieves the three dimensional data set D of the concerned subject and sends it to the ophthalmologic image display device 1. As another implementation example, in the case where the three dimensional data set D is stored in a portable recording medium, a mobile computer, or the like, the three dimensional data set D is read out from the portable recording medium etc. using a reader/writer (described later) of the ophthalmologic image display device 1. The three dimensional data set D thus inputted is stored into the storage device 20 by the controller 10.

The site of the subject's eye represented by the three dimensional data set D is arbitrary, and may include, for example, at least one of the followings: the fundus (e.g., the retina, the choroid, the sclera); the vitreous body; the crystalline lens; the anterior segment (e.g., the cornea, the anterior chamber, the iris, the crystalline lens, the ciliary body, the Zinn's zonule); and an eyelid. Hereinafter, a typical example of the three dimensional data set D will be described wherein the three dimensional data set D is obtained by applying OCT scan to a three dimensional region of the subject's eye that includes part of the fundus and part of the vitreous body.

(Data Input and Output Device 30)

The data input and output device 30 performs input of data into the ophthalmologic image display device 1 and output of data from the ophthalmologic image display device 1. It should be noted that the data input and output device 30 may be configured to perform either one of input or output of data. The data input and output device 30 may include a communication device for sending and receiving data via a communication line such as a LAN, the Internet, a dedicated line, etc. The data input and output device 30 may include a reader/writer for reading data from a recording medium and writing data into a recording medium. Further, the data input and output device 30 may include an image scanner that scans information recorded on a print medium or the like, a printer that records information on a paper medium, or the like.

(Data Processor 40)

The data processor 40 includes a processor that executes the data processing program 23 and performs various data processing. For example, the data processor 40 applies image processing to image data of the subject's eye. As a typical example thereof, the data processor 40 performs rendering such as three dimensional computer graphics (3DCG).

As shown in FIG. 2, the data processor 40 includes the image processor 41. The image processor 41 forms various images based on the three dimensional data set D. For example, based on the three dimensional data set D, the image processor 41 forms a B-mode image, a plurality of front images, and a composite front image. The composite front image is constructed by composing (two or more of) the plurality of front images. The image processor 41 includes the segmentation processor 411, the front image forming device 412, the color converter 413, the composite front image forming device 414, the B-mode image forming device 415, and the segment specifier 416.

The segmentation processor 411 analyzes the three dimensional data set D to specify a plurality of partial data sets corresponding to a plurality of tissues of the subject's eye. Segmentation is image processing for determining specific tissues and/or tissue boundaries and is widely used in the ophthalmologic OCT field. For example, the segmentation processor 411 determines the gradients of the pixel values or voxel values (i.e., brightness values) in each A-mode image included in the three dimensional data set D, and specifies a position where a gradient value is large to be a tissue boundary. Note that an A-mode image is one dimensional image data extending in the depth direction of the fundus. Here, the depth direction of the fundus is defined as, for example, the Z direction, the incident direction of the OCT measurement light, the axial direction, the optical axis direction of the objective lens, or the like.

In a typical example, the segmentation processor 411 specifies a plurality of partial data sets corresponding to a plurality of layer tissues of the fundus by analyzing the three dimensional data set D representing the fundus (e.g., the retina, the choroid) and the vitreous body. Each of the partial data sets is defined by the boundary of layer tissues. Examples of the layer tissue specified as a partial data set include sub-tissues of the retina such as the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer. As another example, it is possible to specify a partial data set corresponding to the Bruch membrane, the choroid, the sclera, the vitreous body, or the like. It is also possible to specify a partial data set corresponding to a lesion part. Examples of lesion parts include a detachment part, an edema, a hemorrhage site, a tumor, a drusen, and the like.

The front image forming device 412 forms a plurality of front images based on at least part of the plurality of partial data sets specified by the segmentation processor 411. Each of the front images is an image showing a predetermined slice area of the three dimensional data set D. The slice area has a thickness in the depth direction of the fundus, for example. The slice area is set, for example, by the user or by the ophthalmologic image display device 1.

The slice area may be a region corresponding to one or more of the plurality of partial data sets specified by the segmentation processor 411. For example, it is possible to take account of any of the followings: a slice area including the partial data set group corresponding to the area from the inner limiting membrane (ILM) to the inner plexiform layer (IPL), which is referred to as a surface layer portion; a slice area including the partial data set group corresponding to the area from the outer nuclear layer (ONL) to the retinal pigment epithelium (RPE), which is referred to as a retinal outer layer portion; and a slice area including the partial data set group corresponding to the choroid that is the area from the Bruch membrane (BM) to the choroid-sclera interface (CSI). Like this, the thickness of a slice area (e.g., the distance between the boundaries in the Z direction) is not necessarily constant, but it is also possible to set a slice area of a constant thickness.

The front image forming device 412 forms a front image by projecting data included in the slice area in the depth direction (i.e., the Z direction). Such a projection front image is referred to as a shadowgram. The projection front image that spans the entire area in the Z direction of the three dimensional data set D is referred to as a projection image, and is used for the registration between a fundus photograph and the three dimensional data set D or like processing. In addition, the front image forming device 412 can also set a C-mode image that represents a transverse cross section (or, a XY cross section or a horizontal cross section) of the three dimensional data set D, as the front image. Further, the front image may be an arbitrary MPR image. For example, the MPR image may be an image of a cross section that is slightly tilted against the XY plane.

The front image formed by the front image forming device 412 may be an arbitrary type of OCT image. The OCT image may be an image representing the morphology of the subject's eye (i.e., ordinary OCT image), a blood vessel enhanced image (i.e., angiogram), or a blood flow dynamic image (i.e., phase image), for example. In addition, the front image forming device 412 can also form a front image by flattening the slice area corresponding to the layer (or layer boundary) specified by the segmentation processor 411 in parallel to the XY plane. The front image thus formed is referred to as a flattened image.

The color converter 413 converts at least one of the plurality of front images formed by the front image forming device 412 from a grayscale image to a color image. The color converter 413 replaces values (i.e., brightness values) of the pixels of at least part of the front image with color values. The color values may be a constant value or values over a predetermined range. In addition, the color converter 413 can perform processing of selecting pixels to be subjected to color conversion. The selection processing may include, for example, arbitrary kinds of image processing such as thresholding on brightness values, shape analysis (e.g., pattern analysis, pattern matching), binarization, or filtering.

A specific example will be described. Suppose that the front image is a blood vessel enhanced image (i.e., angiogram). Although not intended to be limiting, pixels corresponding to blood vessels in a typical blood vessel enhanced image are expressed by relatively high brightness values. In other words, pixels corresponding to blood vessels are expressed in whitish tone (i.e., bright tone) on a blackish background. The color converter 413 extracts pixels having relatively high brightness values from among the pixels included in the front image by applying image processing such as thresholding, binarization, or high pass filtering. The pixels having relatively high brightness values are referred to as high brightness pixels. Further, the color converter 413 replaces the brightness value of each extracted pixel with a predetermined color value. The color represented by the color value is a color that has been assigned to the concerned front image in advance. As will be described in detail later, the color assigned to the front image may be the same as (or similar to) the display color of the frame portion (or rim portion) of the display region in the GUI screen on which the concerned front image is displayed. In addition, the same color value may be given to all the high brightness pixels, or different color values may be given to the high brightness pixels according to the magnitudes of the brightness values thereof, for example. In the former case, a predetermined color value (i.e., default value) is given. As an example of the latter, color conversion using a color palette (i.e., color lookup table or color map) for a pseudo color display can be employed.

The composite front image forming device 414 composes a plurality of front images including at least part of one or more front images converted into color images by the color converter 413. The image constructed in this way is referred to as a composite front image. The registration between the plurality of front images to be composed is unnecessary since all the plurality of front images are constructed from the same three dimensional data set D. In an alternative example, it is possible to apply, to the plurality of front images, natural registration on the basis of the locations of the plurality of front images (i.e., the locations of the plurality of slice areas) in the three dimensional data set D.

The composite front image represents objects, such as blood vessels, lesion parts, layer tissues, in the plurality of slice areas. Here, a mode of expressing the objects can be changed according to the positional relationship between the plurality of slice areas. For example, it is possible to preferentially present the objects in the slice area(s) near the surface of the fundus (i.e., near the inner limiting membrane). At least part of the objects expressed in the composite front image (e.g., blood vessels in a slice area with which color values are associated) are displayed in color.

As described above, in the case where the composite front image display controller 113 displays the plurality of front images one over another by using the layer display function or the like, the composite front image forming device 414 is not provided or the operation of the composite front image forming device 414 is deactivated. In addition, the process related to the opacity (i.e., a values) of the layers is an alternative to the preferential presentation according to slice areas (described above).

The B-mode image forming device 415 forms a B-mode image representing a vertical cross section that has been set in advance, based on the three dimensional data set D. Here, a vertical cross section is a cross section orthogonal to a horizontal cross section. The B-mode image formation may include any known image processing such as MPR.

The segment specifier 416 specifies the partial region of the B-mode image formed by the B-mode image forming device 415 that corresponds to the slice area (i.e., segment) of the three dimensional data set D represented by a front image formed by the front image forming device 412. This front image is typically a front image used to form the composite front image. The specification of the partial region corresponds to the determination of the region that is commonly included in the slice area and the vertical cross section of the B-mode image.

The functions of the data processor 40 are not limited to those mentioned above. For example, the data processor 40 may be capable of performing any of the functions that will be described below or any known functions.

(Operation Device 50)

The operation device 50 is used by the user to input instructions to the ophthalmologic image display device 1. The operation device 50 may include a known operation device usable together with a computer. For example, the operation device 50 may include a pointing device such as a mouse, a touch pad or a track ball. The operation device 50 may include a keyboard, a pen tablet, a dedicated operation panel, or the like. In the case where the ophthalmologic image display device 1 is connected to an ophthalmologic apparatus (e.g., OCT apparatus), an instruction can be input to the ophthalmologic image display device 1 by using an operation device (e.g., a joystick, a button, a switch) provided in the ophthalmologic apparatus. In that case, the operation device 50 includes such an operation device of the ophthalmologic apparatus.

[Display Screen and Usage Mode]

A typical usage mode of the ophthalmologic image display device 1 will be described together with an example of the display screen. In the following example, the controller 10 displays the GUI screen etc. based on the GUI template 21 and the display control program 22. In addition, the controller 10 displays images etc. according to the display control program 22. In addition, the data processor 40 executes various kinds of processing according to the data processing program 23.

First, the user (e.g., medical doctor) of the ophthalmologic image display device 1 inputs an instruction to begin the use of the GUI. Upon receiving the instruction, the display controller 11 (the GUI display controller 111 therein) activates the display control program 22 and displays the GUI screen on the display device 2 based on the GUI template 21. The user inputs a patient ID to the GUI screen using the operation device 50. Alternatively, the ophthalmologic image display device 1 receives the patient ID by reading a patient card or the like with a card reader included in the data input and output device 30. The method of entering patient IDs is not limited to those described here. In some cases, the input operation of patient IDs is not necessary as in the case where the three dimensional data set D stored in a recording medium is input to the ophthalmologic image display device 1, for example.

The controller 10 controls the communication device included in the data input and output device 30 to send the inputted patient ID to the image management server via the network. The image management server receives the patient ID, searches for the image data associated with the patient ID, and transmits the retrieved image data to the ophthalmologic image display device 1. By these processes, for example, all or some pieces of image data acquired in the past for the concerned subject's eye (and the fellow eye of the concerned patient) are retrieved and transmitted. The image data transmitted from the image management server includes the three dimensional data set D.

The communication device included in the data input and output device 30 receives the image data transmitted from the image management server. The controller 10 stores the received image data together with the patient ID into the storage device 20. With this, the image data including at least the three dimensional data set D is stored in the storage device 20. It should be noted that in the present example, the three dimensional data set D is considered to be image data representing a three dimensional region of the eye fundus and the three dimensional region is considered to be represented in the image data of the fundus image (i.e., fundus photograph).

The GUI display controller 111 displays a list of image data of the concerned subject's eye (or of the concerned patient) on the GUI screen. The user selects desired image data using the operation device 50. Here, it is assumed that the three dimensional data set D is selected. The controller 10 reads out the selected three dimensional data set D from the storage device 20 and sends the three dimensional data set D to the data processor 40.

Figure 3:
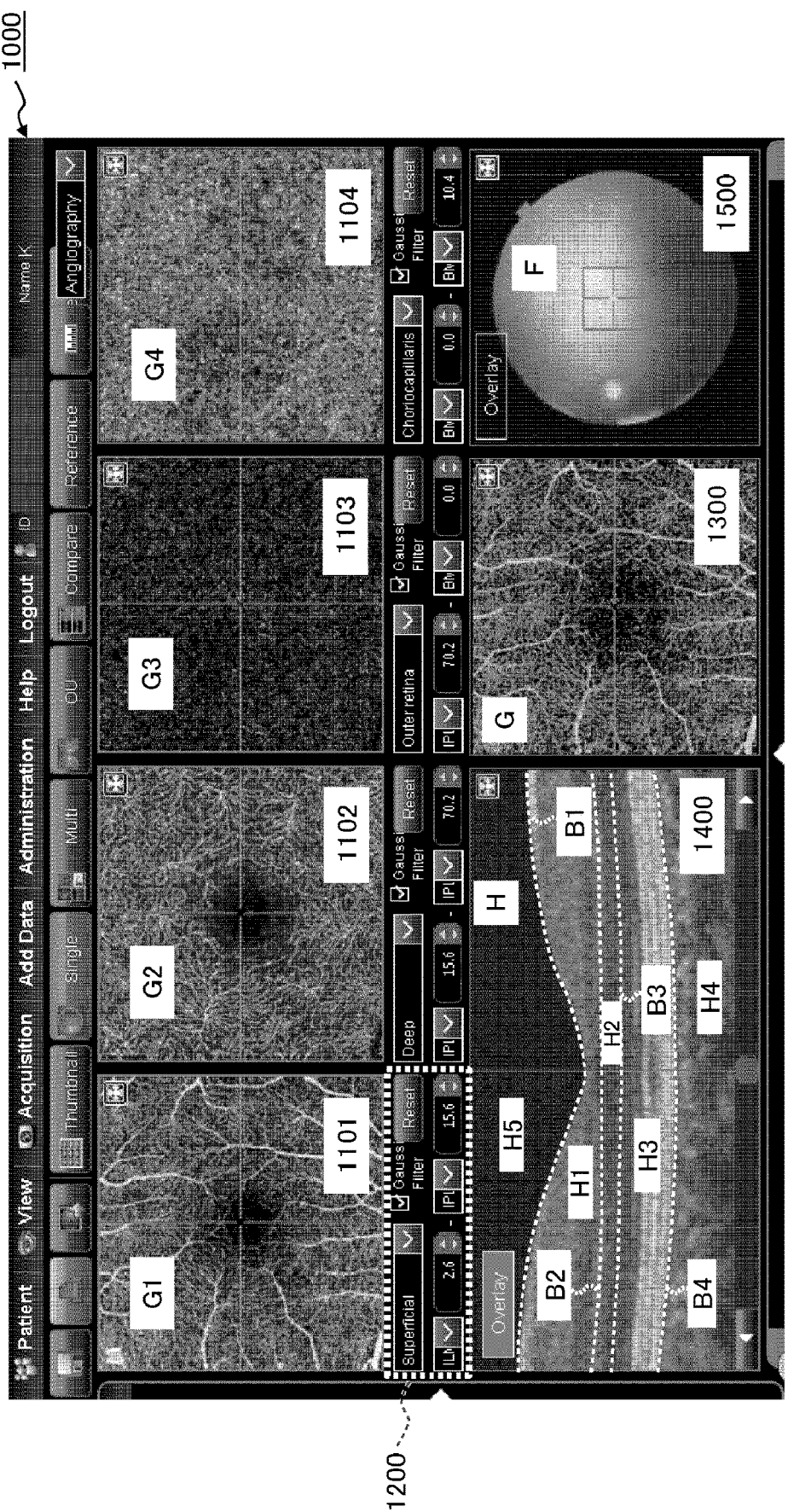
FIG. 3 is a schematic diagram illustrating an example of a screen displayed by the ophthalmologic image display device according to the embodiment.

In the present example, the GUI screen 1000 shown in FIG. 3 is displayed on the display device 2 at this stage. A plurality of image display regions is provided together with various software keys in the GUI screen 1000. More specifically, the plurality of image display regions includes four image display regions provided in the upper row and three image display regions provided in the lower row.

In the four image display regions 1101 to 1104 arranged in the upper row, front images constructed based on the three dimensional data set D are displayed. The four image display regions 1101 to 1104 are referred to as front image display regions. The frame portions (or rim portions) of the front image display regions 1101 to 1104 are displayed in respective colors that are predetermined. The colors of the four frame portions are all different. For example, the frame portions of the front image display regions 1101 to 1104 are displayed in orange, yellowish green, sky blue, and blue, respectively.

The condition setting part 1200 for setting conditions related to front images is provided below each of the front image display regions 1101 to 1104. The condition setting part 1200 includes various software keys. The condition setting part 1200 of the present example includes the following software keys: a pull-down menu for selecting a slice area to be imaged, from among prepared options (e.g., Superficial, Deep, Outer retina, Choriocapillaris); a check box for selecting whether or not to apply a Gaussian filter; a pull-down menu for selecting a layer (or a boundary) of eye fundus that is to be the upper edge of a slice area; an offset display section and an up-down button for moving the position of the upper edge in the depth direction (i.e., Z direction); a pull-down menu for selecting a layer (or a boundary) of eye fundus that is to be the lower edge of a slice area; an offset display section and an up-down button for moving the position of the lower edge in the depth direction; and a reset button to reset current setting contents. Typical examples of options for the upper edge and the lower edge of a slice area include inner limiting membrane (ILM), boundary between nerve fiber layer and ganglion cell layer (NFL/GCL), boundary between inner plexiform layer and inner nuclear layer (IPL/INL), photoreceptor inner segment/outer segment junction (IS/OS), retinal pigment epithelium (RPE), Bruch membrane (BM), and choroid/sclera interface (CSI). The user can set a desired boundary (here, a tissue and a tissue boundary are collectively referred to as a boundary) using both the upper edge pull-down menu and the lower edge pull-down menu. In addition, the user can set the offset of the upper edge and the offset of the lower edge by operating the up-down buttons with referring to a B-mode image etc. The region in the three dimensional data set D corresponding to the boundary set in this way is identified based on the result of segmentation of the three dimensional data set D.

In the lower row, the B-mode image display region 1400, the composite front image display region 1300, and the fundus image display region 1500 are arranged in this order from the left side.

At this stage, no images of the subject's eye are displayed on the GUI screen 1000. However, a fundus image may already be displayed in the fundus image display region 1500 at this stage.

The B-mode image forming device 415 of the data processor 40 forms a B-mode image based on the three dimensional data set D. The setting of a cross section for the formation of a B-mode image is carried out by the user or the B-mode image forming device 415. The B-mode image display controller 114 displays the formed B-mode image H in the B-mode image display region 1400 (see FIG. 3). The user can perform operations for changing the B-scan plane. For example, the user can move the slider provided below the B-mode image display region 1400 in the left-right direction to perform parallel translation of the B-scan plane. The B-mode image forming device 415 forms a new B-mode image representing a cross section corresponding to the position of the slider moved. The B-mode image display controller 114 updates the B-mode image H with the new B-mode image.

The segmentation processor 411 applies segmentation to the three dimensional data set D. In the present example, the segmentation is executed to specify a plurality of partial data sets corresponding to a plurality of layer tissues of retina, one or more partial data sets corresponding to choroid, and one or more partial data sets corresponding to vitreous body. The B-mode image display controller 114 can change the display modes of the image regions in the B-mode image H corresponding to the layer tissues and/or the boundaries specified by the segmentation.

The user can refer to the B-mode image H to set a desired slice area. When a condition such as a slice area is set using the condition setting part 1200, the front image forming device 412 forms a front image based on the set slice area. The front image display controller 112 displays the formed front image in the front image display region corresponding to the concerned condition setting part 1200, that is, in one of the front image display regions 1101 to 1104 arranged above the concerned condition setting part 1200. Through the repetitive performance of such operations and processing, the front images G1 to G4 are displayed in the front image display regions 1101 to 1104, respectively (see FIG. 3).

The color converter 413 converts at least one front image of the four front images G1 to G4, which are gray scale images, into a color image. The color conversion is applied to whole or part of the front image. The color given to the front image is the same as that of the frame portion of the front image display region in which the front image is displayed. For example, The color converter 413 performs one or more of the following four processes: assigning orange color, which is the same color as the frame portion of the front image display region 1101, to the pixels of the blood vessel regions in the front image G1; assigning yellowish green color, which is the same color as the frame portion of the front image display region 1102, to the pixels of the blood vessel regions in the front image G2; assigning sky blue color, which is the same color as the frame portion of the front image display region 1103, to the pixels of the blood vessel regions in the front image G3; and assigning blue color, which is the same color as the frame portion of the front image display region 1104, to the pixels of the blood vessel regions in the front image G4.

The composite front image forming device 414 forms a composite front image by composing a plurality of front images that includes part or all of the front image(s) converted into a (partial) color images by the color converter 413. The process of forming a composite front image will be described with referring to FIG. 4 and FIG. 5. Note that geometric figures are drawn in FIG. 4 and FIG. 5 in place of images of subject's eye to facilitate understanding of the explanation.

Figure 4:
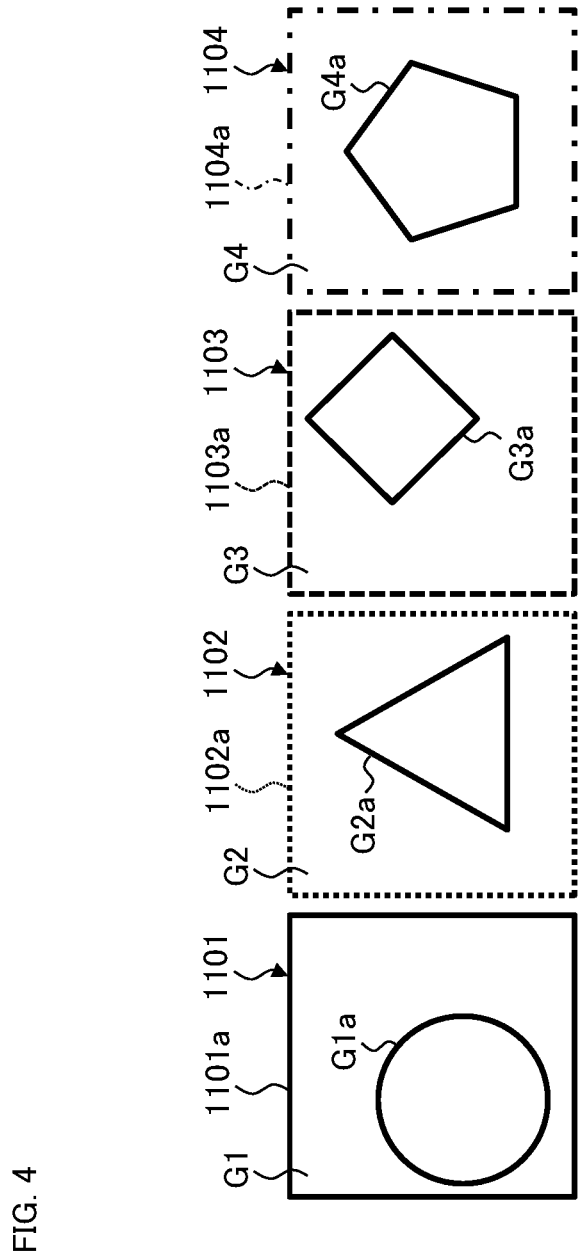
FIG. 4 is a schematic diagram for describing an example of a screen displayed by the ophthalmologic image display device according to the embodiment.

The frame portion 1101a of the front image display region 1101 is displayed in orange color, and the front image G1 in which the circle G1a is drawn is displayed in the frame portion 1101a, as shown in FIG. 4. The frame portion 1102a of the front image display region 1102 is displayed in yellowish green color, and the front image G2 in which the triangle G2a is drawn is displayed in the frame portion 1102a. The frame portion 1103a of the front image display region 1103 is displayed in sky blue color, and the front image G3 in which the rhombus (diamond) G3a is drawn is displayed in the frame portion 1103a. The frame portion 1104a of the front image display region 1104 is displayed in blue color, and the front image G4 in which the pentagon G4a is drawn is displayed in the frame portion 1104a.

The composite front image forming device 414 composes the three front images G1 to G3 out of the four front images G1 to G4. Orange color is assigned by the color converter 413 to the pixels corresponding to the circle G1a in the front image G1 (i.e., high brightness pixels). Yellowish green color is assigned by the color converter 413 to the pixels corresponding to the triangle G2a in the front image G2 (i.e., high brightness pixels). Sky blue color is assigned by the color converter 413 to the pixels corresponding to the rhombus G3a in the front image G3 (i.e., high brightness pixels).

Figure 5:
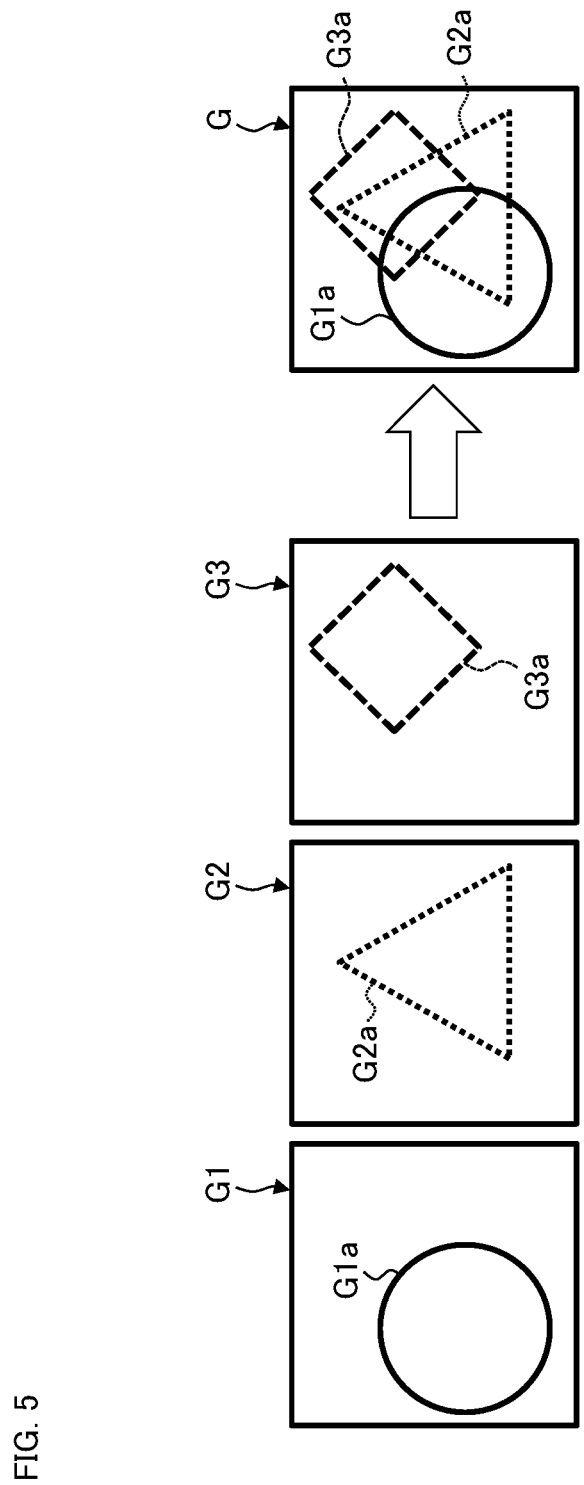
FIG. 5 is a schematic diagram for describing an example of a screen displayed by the ophthalmologic image display device according to the embodiment.

The composite front image forming device 414 composes such three front images G1 to G3 (see FIG. 5). The image composition gives the composite front image G in which the circle G1a expressed in orange color, the triangle G2a expressed in yellowish green color, and the rhombus G3a expressed in sky blue color are depicted. The composite front image display controller 113 displays the composite front image G formed in this way in the composite front image display region 1300. In the case where the three front images G1 to G3 shown in FIG. 3 are composed, since the front images G1 to G3 are blood vessel enhanced images (i.e., angiograms) at different depth positions, the resulting composite front image G includes the blood vessel regions in the front image G1 expressed in orange color, the blood vessel regions in the front image G2 expressed in yellowish green color, and the blood vessel regions in the front image G3 expressed in sky blue color. In other words, the blood vessels located at various depths are represented so as to be distinguishable by the colors corresponding to the different depth positions.

The segment specifier 416 specifies the partial regions of the B-mode image H respectively corresponding to the slice areas (i.e., segments) of the front images G1 to G4. The segment display controller 115 displays the multiple pieces of segment information indicating the partial regions of the B-mode image H specified by the segment specifier 416, on the B-mode image H. Each piece of segment information is displayed in the color that is assigned to the corresponding front image.

FIG. 3 shows a display example of the segment information. In the present example, the slice area of the front image G1 is set to "Superficial", the slice area of the front image G2 is set to "Deep", the slice area of the front image G3 is set to "Outer retina", and the slice area of the front image G4 is set to "Choriocapillaris".

The slice area of the front image G1 corresponds to the partial region H1 having the boundary B1 as the upper edge and the boundary B2 as the lower edge, and the partial region H1 is presented in orange color, which is the same as the color of the frame portion 1101a, as the segment information representing it. The slice area of the front image G2 corresponds to the partial region H2 having the boundary B2 as the upper edge and the boundary B3 as the lower edge, and the partial region H2 is presented in yellowish green color, which is the same as the color of the frame portion 1102a, as the segment information representing it. The slice area of the front image G3 corresponds to the partial region H3 having the boundary B3 as the upper edge and the boundary B4 as the lower edge, and the partial region H3 is presented in sky blue color, which is the same as the color of the frame portion 1103a, as the segment information representing it. The slice area of the front image G4 corresponds to the partial region H4 having the boundary B4 as the upper edge, and the partial region H4 is presented in blue color, which is the same as the color of the frame portion 1104a, as the segment information representing it. It should be noted that the reference symbol "H5" denotes the partial region corresponding to the vitreous body.

Here, it is not necessary to present the segment information for all of the front images G1 to G4. For example, the pieces of segment information can be presented only for the front images G1 to G3 that have been used for the formation of the composite front image G.

The user can designate a desired front image from among the front images G1 to G4. The designation of a desired front image(s) is performed by clicking one or more front images using the pointing device included in the operation device 50, for example. The segment display controller 115 displays only one or more pieces of the segment information respectively corresponding to the one or more front images designated. For example, when the front image G1 is designated, segment information is given only to the partial region H1 corresponding to the designated front image G1 (that is, it is displayed in orange color), and the other partial regions H2 to H5 are displayed in gray scale. As a result, it is possible to easily grasp the segment corresponding to the front image of interest. Note that the segment corresponding to the designated front image may be displayed in a pseudo color so that this segment can be observed in detail.

The user can select front images to be used for forming a composite front image. This selection is made, for example, by clicking two or more front images using the pointing device included in the operation device 50. It is also possible to delete or replace any of the front images used to form the current composite front image, or to add a new front image. The composite front image forming device 414 forms a new composite front image based on a new combination of front images (including the front image to which color conversion has been applied). The composite front image display controller 113 displays the new composite front image in place of the current composite front image. As a result, it becomes possible for the user to observe the new composite front image formed based on the combination of front images designated by the user.

The selection of a front image can be automated. For example, the selection of a front image can be performed based on the slice area having been set. As a specific example, when a part of the choroid, a part of the vitreous body, or the like is designated as a slice area, the designated slice area can be excluded from the subject of the formation of a composite front image. Many small blood vessels are distributed in the choroid and thus, when a color is assigned to the blood vessel regions, the whole front image seems to be lightly colored, which may hinder the grasp of the distribution of blood vessels of the retina. In general, the vitreous body is not necessarily imaged for observation of blood vessels of eye fundus. On the other hand, when observing abnormality of the vitreous body such as vitreous traction, a composite front image that includes a slice area including part of the vitreous body can be constructed. In addition, a composite front image that includes a slice area including part of the vitreous body can be constructed in the case where it is desired to observe the contact surface between the vitreous body and the retina or the vitreous body in the vicinity of the retina. Further, it is possible to switch slice areas, which are used for the formation of a composite front image, according to the type of the three dimensional data set D (e.g., a blood vessel enhanced image, a morphological image, a blood flow dynamic image).

The user can change the slice area of any of the current front images G1 to G4 as desired. The condition setting part 1200 is used to change the slice area. The user sets a desired slice area by operating software keys in the condition setting part 1200 using the pointing device (e.g., the mouse) included in the operation device 50.

For example, when the slice area of the front image G1 is changed, the front image forming device 412 forms a new front image based on the slice area updated. The front image display controller 112 displays the new front image in place of the current front image G1.

In addition, the color converter 413 assigns the color corresponding to the front image G1 (orange color in this case) to part of the new front image. The part of the new front image is blood vessel regions in the new front image, for example. The composite front image forming device 414 uses the new front image in place of the front image G1 to form a new composite front image. The composite front image display controller 113 displays the new composite front image in place of the current composite front image G. In the new composite front image, the blood vessel regions etc. in the new front image is expressed in the same color as that of the front image G1 before the updating.

Further, the segment specifier 416 newly determines the partial region of the B-mode image H corresponding to the slice area of the new front image. The segment display controller 115 displays new segment information indicating the newly specified partial region in place of the segment information corresponding to the current front image G1.

According to such a configuration, it becomes possible to automatically executing the updating of the front image, the updating of the composite front image, and the updating of the segment information, in response to any change in the slice area of the front image.

Actions and Effects

Actions and effects of the ophthalmologic image display device according to the embodiment will be described.

The ophthalmologic image display device (1) of the embodiment includes a storage device (20), an image processor (41), and a display controller (11). The storage device (20) stores a three dimensional data set (D) acquired by scanning a subject's eye using OCT. Based on the three dimensional data set (D), the image processor (41) forms a B-mode image (H), a plurality of front images (G1 to G4), and a composite front image (G) constructed by composing the plurality of front images (G1 to G4). The display controller (11) displays the B-mode image (H), the plurality of front images (G1 to G4), and the composite front image (G) in a predetermined layout on a display device (the display device 2). The GUI screen 1000 of the above embodiment provides an example of the display layout of these images.

The display controller (11) displays distinguishment color information (colors of the frame portions 1101a to 1104a) for the distinguishment between the plurality of front images (G1 to G4) by colors. Further, the display controller (11) displays slice area information (presentation colors of the partial regions H1 to H4) that indicates partial regions (H1 to H4) of the B-mode image (H) corresponding to a slice area of the three dimensional data set (D) represented by each of the plurality of front images (G1 to G4) in a color according to the distinguishment color information. In addition, the display controller (11) displays a composite front image (G) based on at least one of the plurality of front images (G1 to G4), each of which is expressed by a color according to the distinguishment color information.

According to such an embodiment, when observing a plurality of front images, the user can grasp the positions (e.g., depth positions) of the front images and the positional relationships between the front images with the slice area information. In addition, the user can grasp the states and distributions of objects (e.g., blood vessels, lesion parts, layer tissues) at various depth positions with the composite front image. Therefore, the embodiment makes it possible for the user to easily and comprehensively grasp the states of the subject's eye at various depth positions.

The embodiment may include a first operation device (the operation device 50). When an operation for changing a slice area of a first front image, which is one of the plurality of front images (G1 to G4), to a new slice area has been performed using the first operation device, the image processor (41) forms a new front image based on the new slice area, and replaces the first front image with the new front image to form a new composite front image. In addition, the display controller (11) executes control to display new slice area information that indicates a partial region of a B-mode image corresponding to the new slice area, to display the new front image in place of the first front image, and to display the new composite front image in place of the composite front image.

According to such a configuration, the user can display a front image of a desired slice area. Further, in response to the change of the slice area, a front image corresponding to a new slice area is automatically displayed, a new slice area information that indicates the new slice area is automatically displayed, and a new composite front image formed based on the new front image is automatically displayed. In this manner, various kinds of images and information are automatically updated in response to the change of the slice area. Therefore, the embodiment makes it possible for the user to easily observe desired depth positions.

Note that in the present example, the display controller (11) can display the new slice area information with a color according to distinguishment color information corresponding to the first front image. In other words, even though the slice area information is updated in response to the change of the slice area, the display color of the slice area information before the updating and that after the updating can be the same. Further, the first operation device may include a pointing device (e.g., a mouse) for performing an operation of the slice area information or the B-mode image.

The embodiment may include a second operation device (the operation device 50). When an operation for designating a second front image from among the plurality of front images (G1 to G4) has been performed using the second operation device, the display controller (11) can execute control to display only slice area information corresponding to the second front image among a plurality of pieces of slice area information corresponding to the plurality of front images (G1 to G4).

According to such a configuration, the user can easily and clearly grasp the slice area of a desired front image.

In the embodiment, the image processor (41) may be configured to assign a color according to the distinguishment color information to a high brightness pixel in each of the plurality of front images (G1 to G4) and compose at least one of the plurality of front images (G1 to G4) to form the composite front image (G).

According to such a configuration, it becomes possible to provide color-coded display of an object that is expressed with relatively high brightness, in accordance with the position (e.g., the depth position) of the slice area. The present example is effective for observing blood vessels and lesion parts.

The embodiment may include an image selection device for selecting two or more front images from among the plurality of front images. In the above embodiment, for example, a part of the controller 10 functions as an image selection device. The image selection device includes a processor that operates according to a computer program therefor. The image selection device may be configured to automatically select a front image with referring to a predetermined attribute. Examples of the attribute include the type of slice area, and the type of three dimensional data set. Alternatively, the image selection device may be configured to select a front image in accordance with an instruction (i.e., operation) from a user. In these ways, the selection of front image in the present example may be automatic or manual. The image processor (41) forms an other composite front image based on the two or more front images selected by the image selection device. The display controller (11) displays the other composite front image that is newly formed, in place of the composite front image (G) currently displayed.

According to such a configuration, a new composite front image can be automatically formed from two or more front images selected automatically or manually, and the display of the composite front image can be automatically updated. Therefore, the embodiment makes it possible to facilitate the observation work.

In the embodiment, the image processor (41) may include a segmentation processor (411) and a front image forming device (412). The segmentation processor specifies a plurality of partial data sets corresponding to a plurality of tissues of the subject's eye, by analyzing the three dimensional data set. The front image forming device forms a plurality of front images based on at least part of the plurality of partial data sets specified.

In addition, the image processor (41) may further include a partial region specifier (the segment specifier 416) that specifies a partial region (H1 to H4) of a B-mode image (H) corresponding to a slice area of each of at least one of the plurality of front images (G1 to G4) formed by the front image forming device (412).

According to such a configuration, processing of forming a front image of a stratified tissue such as eye fundus can be performed in an appropriate manner. For example, it is possible to provide a front image representing a single layer tissue or a front image representing a combination of two or more layer tissues. In addition, the present configuration makes it possible for the user to easily grasp the position of the layer tissue and the positional relationship between the layer tissues by referring to the B-mode image. The present configuration can also be applied to any ocular tissues other than such a stratified tissue.

In the embodiment, the distinguishment color information for the distinguishment between the plurality of front images (G1 to G4) by colors may include colors given to respective frame portions (1101a to 1104a) of a plurality of display regions (1101 to 1104) in which the plurality of front images (G1 to G4) is respectively displayed.

Note that the distinguishment color information is not limited to such an exemplary aspect, and the aspect of the distinguishment color information is optional as long as the plurality of front images (G1 to G4) can be distinguished by colors. As another example, the distinguishment color information may include display colors of the plurality of front images (G1 to G4) themselves.

For example, it is possible to display a front image in which values of some or all of the pixels have been converted into color values by the color converter 413 of the above embodiment. As a specific example, the front image G1 in which the blood vessel regions are expressed in orange color can be displayed in the front image display region 1101, the front image G2 in which the blood vessel regions are expressed in yellowish green color can be displayed in the front image display region 1102, the front image G3 in which the blood vessel regions are expressed in sky blue color can be displayed in the front image display region 1103, and the front image G4 in which the blood vessel regions are expressed in blue color can be displayed in the front image display region 1104. In the present example, the colors of the blood vessel regions at individual depth positions in the composite front image are the same as the colors of the blood vessel regions in the front image at individual depth positions. This makes it easy to grasp the correspondence between the blood vessel regions in the composite front image and the blood vessel regions in the front image.

As still another example, it is possible to display an icon or image of a predetermined color on or in the vicinity of the front image, or to display a character string (e.g., the name of the color) that represents a color on or in the vicinity of the front image.

The actions and effects of the embodiments are not limited to those described above. The actions and effects provided by the items described as the above embodiments should also be taken into consideration. In addition, the actions and effects provided by the combination of a plurality of items described as the above embodiments should also be taken into consideration.

<Ophthalmologic Imaging Device>

Figure 6:
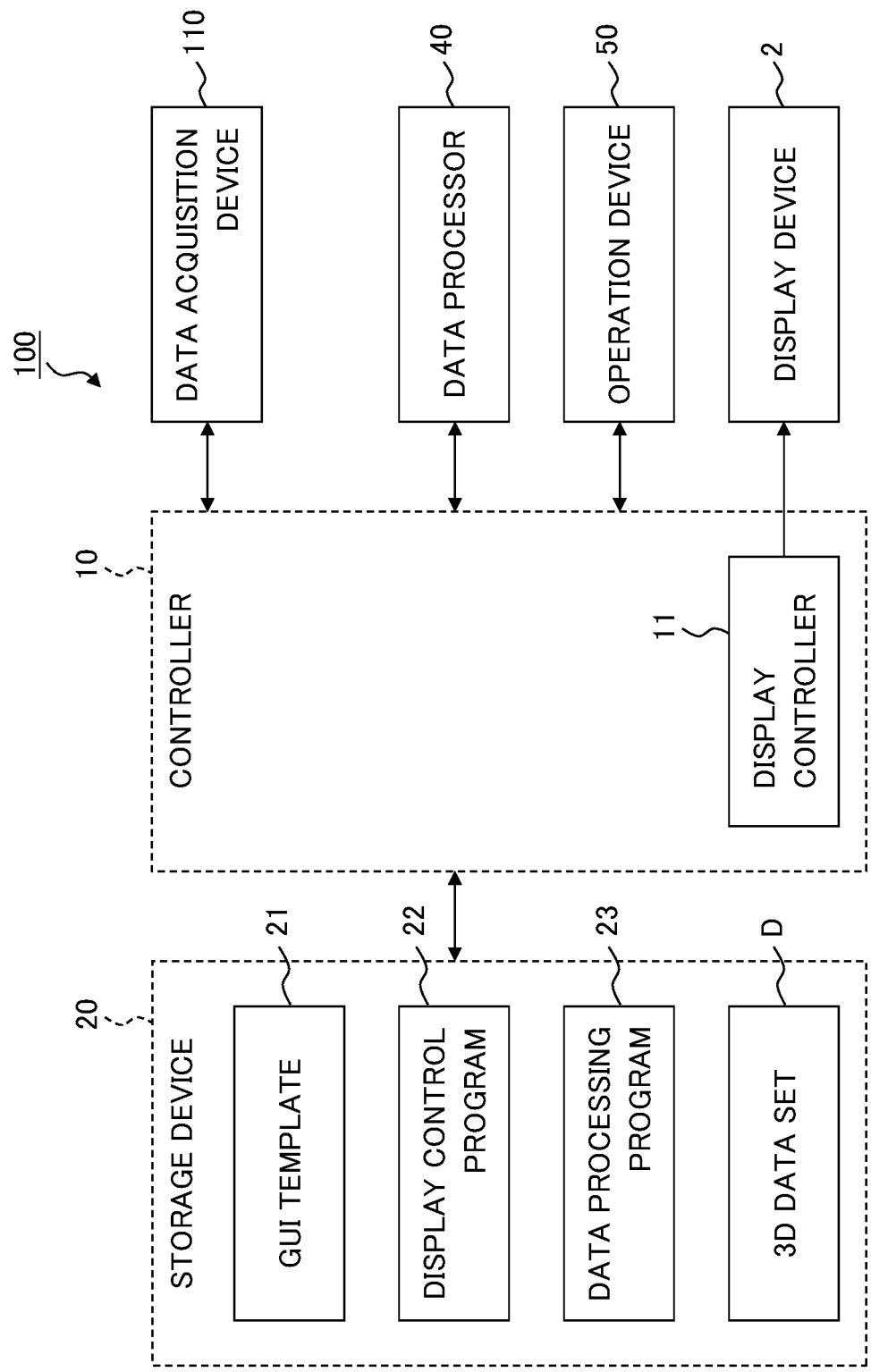
FIG. 6 is a schematic diagram illustrating an example of the configuration of an ophthalmologic imaging device according to an embodiment.

The ophthalmologic imaging device according to the embodiment may include part or all of the components of the ophthalmologic image display device according to the embodiment described above, for example. Exemplary configuration of the ophthalmologic imaging device is shown in FIG. 6. Components similar to those of the ophthalmologic image display device 1 (FIG. 1) of the embodiment described above are denoted by the same reference symbols, and descriptions thereof will be omitted unless otherwise mentioned. The ophthalmologic imaging device 100 shown in FIG. 6 may include part or all of the components shown in FIG. 2. Further, the display screen and the displayed images may be the same as or similar to the aspects shown in FIG. 3. The aspects of the distinguishment color information may be the same as those shown in FIG. 4. In addition, as for data processing such as image processing, it is possible to employ part or all of the processing described with referring to FIG. 4 and FIG. 5, and further, modifications thereof.

The ophthalmologic imaging device 100 has a function of acquiring data on the subject's eye using OCT and a function of displaying various information related to the subject's eye and a GUI for observing the image of the subject's eye on the display device 2. The display device 2 may be a part of the ophthalmologic imaging device 100 or may be an external device connected to the ophthalmologic imaging device 100.

The ophthalmologic imaging device 100 includes the controller 10, the storage device 20, the data processor 40, the operation device 50, and the data acquisition device 110. The controller 10 includes the display controller 11. As in the embodiment described above, the storage device 20 stores the GUI template 21, the display control program 22, the data processing program 23, and the three dimensional data set D. The three dimensional data set D is generated by the data acquisition device 110 and stored in the storage device 20. The controller 10, the storage device 20, the data processor 40 and the operation device 50 may respectively include at least the same functions as those of the ophthalmologic image display device 1 of the embodiment described above.

The data acquisition device 110 acquires a three dimensional data set by applying OCT to the subject's eye. The data acquisition device 110 includes: a configuration for performing measurement using, for example, spectral domain OCT or swept source OCT (e.g., an optical system, a drive system, a control system); and a configuration for forming image data based on the data acquired using OCT (e.g., a processor). The image data forming processing includes processing such as noise removal (and/or noise reduction), filtering, Fast Fourier Transform (FFT) as in the conventional OCT techniques, for example.

The data acquisition device 110 scans a three dimensional region of the subject's eye. The scanning mode is, for example, raster scan (also referred to as three dimensional scan). This raster scan is performed, for example, so as to scan each of a plurality of B-cross sections a predetermined number of times. That is, the raster scan is performed, for example, so as to scan a plurality of B-cross sections in a sequential manner, each a predetermined number of times. The data acquisition device 110 forms a plurality of cross sectional images (i.e., B-mode images) for each of the B-cross sections based on the data acquired by the raster scan. By embedding these cross sectional images in a single three dimensional coordinate system, stack data is formed. In the stack data, a predetermined number of cross sectional images is assigned to each of the B-cross sections. In addition, volume data (also referred to as voxel data) is formed by applying interpolation processing or the like to the stack data. For the volume data as well, a predetermined number of voxel groups are assigned to the position corresponding to each of the B-cross sections. Stack data and volume data are examples of the three dimensional data set D. The three dimensional data set D constructed in the above manner is stored in the storage device 20 by the controller 10.

Based on the three dimensional data set D thus obtained, the ophthalmologic imaging device 100 provides the GUI, control and data processing as in the case of the ophthalmologic image display device 1 according to the embodiment described above. Based on the three dimensional data set D, the data processor 40 forms a B-mode image, a plurality of front images, and a composite front image. The composite front image is formed by composing part or all of the front images. The image formation processes may be the same as those performed by the image processor 41 of the embodiment described above (see FIG. 2).

The display controller 11 displays the B-mode image, the plurality of front images and the composite front image formed by the data processor 40 in a predetermined layout on the display device 2. Further, the display controller 11 displays distinguishment color information for the distinguishment between the plurality of front images by colors. Furthermore, the display controller 11 displays slice area information indicating the partial region of the B-mode image corresponding to the slice area in the three dimensional data set D represented by each of the plurality of front images, in a color according to the distinguishment color information. In addition, the display controller 11 displays a composite front image based on the plurality of front images, each expressed by a color corresponding to its distinguishment color information.

In this way, it can be said that the ophthalmologic imaging device 100 includes the data acquisition device (e.g., the OCT function and the OCT image forming function) in addition to the configuration of the ophthalmologic image display device according to the embodiment described above. Further, the ophthalmologic imaging device 100 may include any items (e.g., configurations, controls, actions, effects) related to the ophthalmologic image display device of the embodiment described above.

According to the ophthalmologic imaging device 100 thus configured, like the ophthalmologic image display device 1 of the embodiment described above, it is possible for the user to easily and comprehensively grasp the states of the subject's eye at various depth positions.

Modification Example

The configuration described above is only an example for implementing the present invention. Therefore, any modification (e.g., omission, substitution, replacement, addition) can be appropriately applied within the scope of the gist of the present invention.

For example, in the ophthalmologic image display device and the ophthalmologic imaging device according to the embodiments, the display mode of the colors of the above-described various information is not limited to the monochromatic representation, but may be color gradient representation (or, gradation representation, color ramp representation, color progression representation). For example, part or all of the front image G1 can be displayed in orange color based gradation (e.g., gradation from black to white mixed with orange color), part or all of the front image G2 can be displayed in yellowish green color based gradation (e.g., gradation from black to white mixed with yellowish green color), and part or all of the front image G3 can be displayed in sky blue color based gradation (e.g., gradation from black to white mixed with sky blue color). As the segment information displayed together with the B-mode image H, the partial region H1 can be displayed in orange color based gradation, the partial region H2 can be displayed in yellowish green color based gradation, the partial region H3 can be displayed in sky blue color based gradation, and the partial region H4 can be displayed in blue color based gradation.

Further, it is possible to set gradations according to depth positions. For example, the storage device 212 can store in advance a lookup table in which depth positions (e.g., Z coordinates) are associated with gradations (e.g., gradation values, tone values). By referring to this lookup table, the gradation corresponding to the depth position of a front image can be specified. In addition, part or all of the concerned front image can be displayed in the gradation specified. Further, the segment information displayed together with the B-mode image H can also be displayed in the same gradation mode as the corresponding front image. In the case where the present example is applied, a single color may be assigned to a plurality of front images. In this case, the depth positions of the object depicted in the plurality of front images are distinguished by gradation. As described above, the distinguishment by color in the present invention includes not only a distinguishing method using different colors but also a distinguishing method using gradation. More generally, the distinguishment by color in the present invention also includes a distinguishing method using any color-related characteristics.

The invention claimed is:

1. An ophthalmologic image display device comprising:
   a storage device that stores a three dimensional data set acquired by scanning a subject's eye using optical coherence tomography;
   an image processor that forms, based on the three dimensional data set, a B-mode image, a plurality of front images, and a composite front image obtained by composing the plurality of front images; and
   a display controller that displays the B-mode image, the plurality of front images and the composite front image in a predetermined layout on a display device,
   wherein the plurality of front images includes a plurality of blood vessel enhanced images,
   the image processor assigns, to a pixel corresponding to a blood vessel in each of the plurality of blood vessel enhanced images, a color according to distinguishment color information for distinguishment between the plurality of blood vessel enhanced images by colors, and then composes the plurality of blood vessel enhanced images such that at least a portion of at least two of the plurality of blood vessel enhanced images overlap each other to form the composite front image, and
   the display controller displays the distinguishment color information and slice area information that indicates a partial region of the B-mode image corresponding to a slice area of the three dimensional data set represented by each of the plurality of blood vessel enhanced images in a color according to the distinguishment color information, and displays a composite front image based on the plurality of blood vessel enhanced images, each of which is expressed by a color according to the distinguishment color information.

2. The ophthalmologic image display device of claim 1, further comprising a first operation device, wherein
   when an operation for changing a slice area of a first front image, which is one of the plurality of front images, to a new slice area has been performed using the first operation device, the image processor forms a new front image based on the new slice area, and replaces the first front image with the new front image to form a new composite front image, and
   the display controller displays new slice area information that indicates a partial region of a B-mode image corresponding to the new slice area, displays the new front image in place of the first front image, and displays the new composite front image in place of the composite front image.

3. The ophthalmologic image display device of claim 2, wherein the display controller displays the new slice area information with a color according to the distinguishment color information corresponding to the first front image.

4. The ophthalmologic image display device of claim 2, wherein the first operation device comprises a pointing device for performing an operation of the slice area information or the B-mode image.

5. The ophthalmologic image display device of claim 1, further comprising a second operation device, wherein
   when an operation for designating a second front image from among the plurality of front images has been performed using the second operation device, the display controller displays only slice area information corresponding to the second front image among a plurality of pieces of slice area information corresponding to the plurality of front images.

6. The ophthalmologic image display device of claim 1, wherein the image processor assigns a color according to the distinguishment color information to a high brightness pixel in each of the plurality of front images and composes the plurality of front images to form the composite front image.

7. The ophthalmologic image display device of claim 1, further comprising an image selection device for selecting two or more front images from among the plurality of front images, wherein
   the image processor forms an other composite front image based on the two or more front images, and
   the display controller displays the other composite front image in place of the composite front image.

8. The ophthalmologic image display device of claim 1, wherein the image processor comprises:
   a segmentation processor that specifies a plurality of partial data sets corresponding to a plurality of tissues of the subject's eye by analyzing the three dimensional data set; and
   a front image forming device that forms a plurality of front images based on at least part of the plurality of partial data sets.

9. The ophthalmologic image display device of claim 8, wherein the image processor further comprises a partial region specifier that specifies a partial region of a B-mode image corresponding to a slice area of each of the plurality of front images formed by the front image forming device.

10. The ophthalmologic image display device of claim 1, wherein the distinguishment color information represents colors of frame portions of a plurality of display regions in which the plurality of front images is respectively displayed.

11. The ophthalmologic image display device of claim 1, wherein the distinguishment color information represents display colors of the plurality of front images.

12. An ophthalmologic imaging device comprising:
    a data acquisition device that acquires a three dimensional data set by scanning a subject's eye using optical coherence tomography;
    an image processor that forms, based on the three dimensional data set, a B-mode image, a plurality of front images, and a composite front image obtained by composing the plurality of front images; and
    a display controller that displays the B-mode image, the plurality of front images and the composite front image in a predetermined layout on a display device,
    wherein the plurality of front images includes a plurality of blood vessel enhanced images,
    the image processor assigns, to a pixel corresponding to a blood vessel in each of the plurality of blood vessel enhanced images, a color according to distinguishment color information for distinguishment between the plurality of blood vessel enhanced images by colors, and then composes the plurality of blood vessel enhanced images such that at least a portion of at least two of the plurality of blood vessel enhanced images overlap each other to form the composite front image, and
    the display controller displays the distinguishment color information and slice area information that indicates a partial region of the B-mode image corresponding to a slice area of the three dimensional data set represented by each of the plurality of blood vessel enhanced images in a color according to the distinguishment color information, and displays a composite front image based on the plurality of blood vessel enhanced images, each of which is expressed by a color according to the distinguishment color information.

13. A method of operating an ophthalmologic image display device, the method comprising:

storing a three dimensional data set acquired by scanning a subject's eye using optical coherence tomography;

forming, based on the three dimensional data set, a B-mode image, a plurality of front images, and a composite front image obtained by composing the plurality of front images;

displaying the B-mode image, the plurality of front images and the composite front image in a predetermined layout on a display device, wherein the plurality of front images includes a plurality of blood vessel enhanced images;

assigning, to a pixel corresponding to a blood vessel in each of the plurality of blood vessel enhanced images, a color according to distinguishment color information for distinguishment between the plurality of blood vessel enhanced images by colors;

composing the plurality of blood vessel enhanced images to form the composite front image;

displaying the distinguishment color information and slice area information that indicates a partial region of the B-mode image corresponding to a slice area of the three dimensional data set represented by each of the plurality of blood vessel enhanced images in a color according to the distinguishment color information; and displaying a composite front image based on the plurality of blood vessel enhanced images, each of which is expressed by a color according to the distinguishment color information and at least a portion of at least two of the plurality of blood vessel enhanced images overlap each other in the composite front image.

14. The ophthalmologic image display device of claim 1, wherein each of the plurality of front images corresponds to a different depth position of the subject's eye.

15. The ophthalmologic image display device of claim 1, wherein the at least two of the plurality of blood vessel enhanced images that overlap each other have blood vessels displayed in different colors according to respective distinguishment color information.

* * * * *